United States Patent [19]

Schiffer

[11] Patent Number: 5,195,978
[45] Date of Patent: Mar. 23, 1993

[54] RAPID EXCHANGE OVER-THE-WIRE CATHETER WITH BREAKAWAY FEATURE

[75] Inventor: Michael C. Schiffer, Laguna Hills, Calif.

[73] Assignee: Baxter International Inc., Deerfield, Ill.

[21] Appl. No.: 806,947

[22] Filed: Dec. 11, 1991

[51] Int. Cl.$^5$ .......................................... A61M 5/178
[52] U.S. Cl. ................................. 604/161; 604/280
[58] Field of Search .............. 604/158, 160, 161, 280, 604/164, 282

[56] References Cited

U.S. PATENT DOCUMENTS

| | | | |
|---|---|---|---|
| 4,299,226 | 11/1981 | Banka | 128/344 |
| 4,306,562 | 12/1981 | Osborne | 128/348 |
| 4,323,701 | 4/1982 | Simpson et al. | 128/343 |
| 4,411,654 | 10/1983 | Boarini et al. | 604/161 |
| 4,413,989 | 11/1983 | Schjeldahl et al. | 604/96 |
| 4,545,390 | 10/1985 | Leary | 128/772 |
| 4,585,000 | 4/1986 | Hershenson | 128/345 |
| 4,616,648 | 10/1986 | Simpson | 128/303 R |
| 4,747,833 | 5/1988 | Kousai et al. | 604/161 |
| 4,762,129 | 8/1988 | Bonzel | 128/344 |
| 4,776,846 | 10/1988 | Wells | 604/161 |
| 4,824,435 | 4/1989 | Giesy et al. | 604/49 |
| 4,883,468 | 11/1989 | Kousai et al. | 604/161 |
| 4,973,305 | 11/1990 | Goltzer | 604/158 |
| 4,983,168 | 1/1991 | Moorehead | 604/161 |
| 5,049,131 | 9/1991 | Deuss | 604/280 |
| 5,061,273 | 10/1991 | Yock | 606/194 |

OTHER PUBLICATIONS

Bonzel et al., "The sliding rail system (monorail): . . . ", Z. Kardiol. 76:Suppl. 6, 119–122 (1987).
Gerlock, Jr., M.D., "Essentials of Diagnostic and Interventional Angiographic Techniques", W. B. Saunders Company, 1984, pp. 23–26.
de Feyter et al., "Short term results of percutaneous transluminal coronary angioplasty with the monorail technique . . . ", Br. Heart J., 1990; 63:255-9, pp. 253–259.
Esplugas et al., "False Coronary Dissection With the New Monorail Angioplasty Balloon Catheter", Catheterization and Cardiovascular Diagnosis 19:30–33 (1990).
Nordenstrom, "New Instruments for Catheterization and Angiocardiography", Radiology 85:256–259, 1965.
Bernhard Meier, "Coronary Angioplasty" Grune & Stratton, Inc., 1987, pp. 13–15, 251, 257 and 260.
de Freitas et al., "Percutaneous transluminal coronary angioplasty and determination of intra-coronary gradient with a new 'monorail' system", Rev. Port. Cardiol. 8(10):699–702 (1989).
Nordenstrom, "Balloon Catheters for Percutaneous Insertion into the Vascular System", Acta. Radiology, 57:411, 1962, pp. 411–416.
American Heart Association, "Abstracts From the 59th Scientific Sessions", Circulation Supplement, Part 2, vol. 74, No. 4, Oct. 1986, Monogram No. 124, pp. II459.
Burch et al., "Side Holes in PTCA Guiding Catheters", Catheterization & Cardiovascular Diagnosis 11:552 (1985).
McKinnon, "Simplified Method of Exchanging Clotted Intravascular Catheters", Radiology 106:458, Feb. 1973, p. 458.
Crittenden, "Dilatation balloons: polymer selection, balloon design and assembly", Z. Kardiol. 76: Suppl. 6; 1987, pp. 33–36.
Bonzel et al., "A New Catheter System for Coronary Angioplasty (PTCA) with Exchangeable Intracoronary Catheters, High Flow of Contrast Agent, & Improved Steerability", 1986, pp. 195–199, Biomed. Technik.

*Primary Examiner*—Gene Mancene
*Assistant Examiner*—Frank A. LaViola
*Attorney, Agent, or Firm*—Poms, Smith, Lande & Rose

[57] ABSTRACT

A rapid exchange over-the-wire catheter is disclosed provided with one or more breakaway elements for progressively exposing the guide wire from the proximal end toward the distal end of the catheter in a simple and efficient manner. The breakaway element may be formed as a longitudinally aligned pull strip provided in the catheter guidewire lumen or as one or more linearly arrayed tubular breakaway segments in the catheter shaft or as a combination of both features.

16 Claims, 3 Drawing Sheets

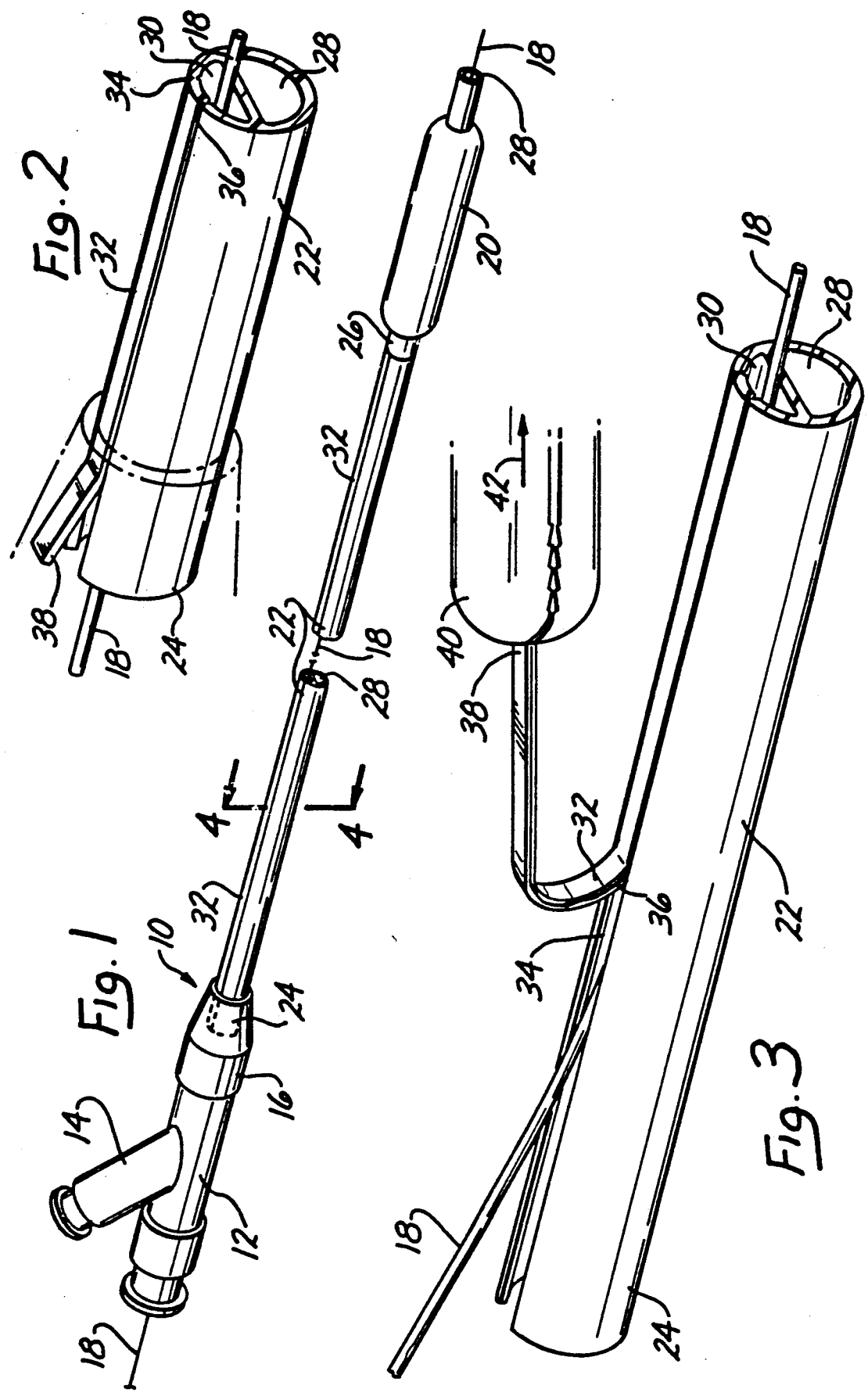

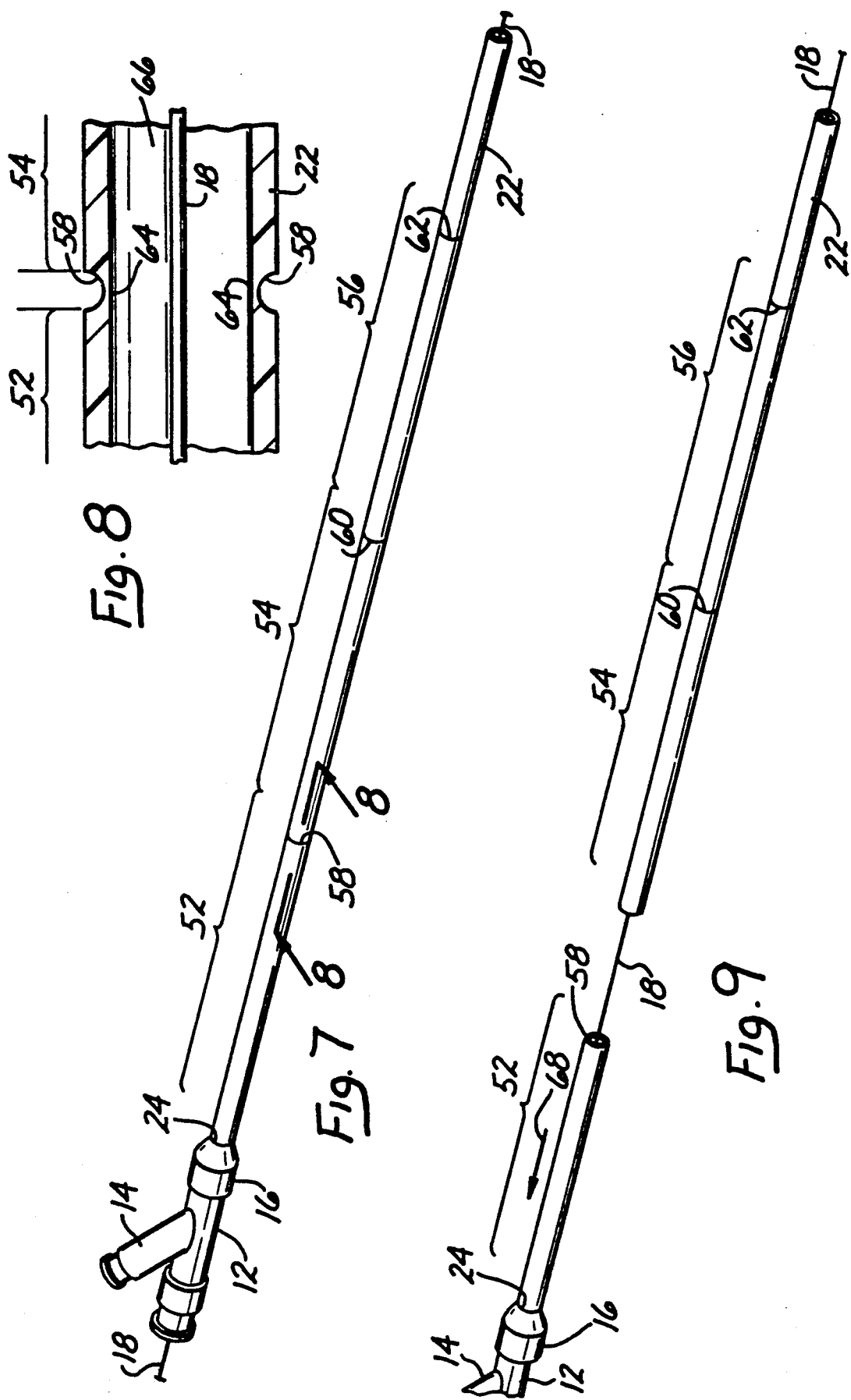

RAPID EXCHANGE OVER-THE-WIRE CATHETER WITH BREAKAWAY FEATURE

FIELD OF THE INVENTION

The present invention relates in general to the field of catheters, especially dilatation or balloon catheters employed in the treatment of vascular diseases. More particularly, the present invention relates to an over-the-wire catheter provided with a breakaway component or feature. This feature may include a pull tab extending along a majority of the length of the catheter guidewire lumen from its proximal opening or adjacent thereto to a position adjacent its distal end and/or one or more linearly arrayed breakaway segments to progressively expose the guidewire and facilitate the removal or exchange of the catheter assembly without docking a guidewire extension or sacrificing guidewire access to a target site.

BACKGROUND OF THE INVENTION

One of the principle goals of modern surgery has been the reduction or elimination of trauma associated with surgical procedures. When surgical invasiveness and trauma are reduced the associated complications are correspondingly reduced. As a result, the less invasive the surgical procedure the greater the chances for a rapid and uncomplicated recovery by the patient. A recent successful development in the field of less invasive surgery is the medical procedure known as angioplasty. Angioplasty has become a widely accepted method for opening obstructions or stenoses throughout the vascular system, particularly in the coronary arteries.

The most common form of angioplasty practiced to date is percutaneous transluminal coronary angioplasty (PTCA). In virtually all forms of PTCA a dilatation catheter having an inflatable balloon at its distal end (the end farthest from the operating physician) is guided through the patient's artery and the balloon is positioned across the stenosis. Once in place the balloon is inflated for a brief period of time in order to displace or deform the occluding lesion. After the stenosis has been opened and adequate blood flow has been reestablished the catheter is withdrawn. In this manner, it is possible to open blocked coronary arteries through a small vascular incision without the serious risks and complications previously associated with open heart surgery.

In most forms of PTCA the dilatation catheter is guided into position through the patient's arteries utilizing a very small diameter flexible guidewire. Typically, guidewires are formed of surgical grade stainless steel having a diameter on the order of 0.010 to 0.015 inches and an overall length of approximately 70 to 75 inches (175 cm). The distal end of the guidewire is extremely flexible and may be formed as a coil of very small diameter wire to enable the cardiac physician to direct the guidewire along the branched and convoluted arterial pathway as the guidewire is advanced to the lesion at the target site. Once the guidewire is positioned across the lesion an appropriately sized dilatation catheter is advanced "over-the-wire" by sliding the tubular lumen of the catheter over the guidewire from its proximal end to its distal end. At this point in the procedure the dilatation balloon is in a deflated configuration having a minimal cross-sectional diameter which facilitates its positioning across the lesion prior to inflation. At various times throughout the procedure radiopaque dyes are injected into the artery to enable the cardiac physician to directly visualize the positioning of the catheter within the target vascular pathway on a fluoroscope.

An undesirable complication associated with the utilization of such "over-the-wire" dilatation catheters is the need to extend the proximal end of the guidewire outside of the patient's body a sufficient distance to enable the over-the-wire catheter to be threaded onto the guidewire without disturbing the positioning of the guidewire distal end at the target lesion. Typically, a guidewire extension is "docked" or affixed to the proximal end of the guidewire in order to provide the additional length necessary to thread the guidewire into the catheter. As the typical dilatation catheter ranges in length from approximately 50-65 inches (120 cm to 160 cm) the guidewire extension can be quite long and awkward to manipulate as it extends outside the patient's body. Alternatively, an exceptionally long guidewire on the order of 120 inches (300 cm) in length may be positioned initially and then exchanged for a shorter, easier to handle guidewire after positioning of the catheter. In either case, additional medical personnel may be necessary solely to monitor or manipulate the guidewire or its extension. Moreover, the junction between the docked guidewire end and the docked extension may interfere with the smooth advancement of the catheter along the guidewire which may decrease the physician's control of the procedure.

A number of dilatation catheter designs have been developed in an attempt to reduce or eliminate these problems. For example, "fixed-wire" dilatation catheters incorporating an internally fixed guidewire or stiffening element have been utilized with some degree of success. In addition to eliminating the need for guidewire extension these fixed-wire designs are smaller in diameter than their over-the-wire counterparts because a single balloon inflation lumen is also utilized to contain the fixed guidewire. As a result, these designs are quite maneuverable and relatively easy to position. However, the most significant drawback associated with fixed-wire catheter designs is the inability to retain guidewire access to the target site when removing or exchanging the catheter. Removal or replacement of a balloon catheter is not an uncommon occurrence during balloon angioplasty. Should it become necessary to perform such a removal or exchange procedure the fixed guidewire must also be removed simultaneously. This greatly complicates reaccessing the lesion with a subsequent device if necessary.

An additional drawback associated with fixed-wire catheter designs is the inability to exchange the guidewire. Though relatively rare, in some instances replacement of a broken or defective guidewire is necessary. With these fixed wire unitary designs the entire assembly must be removed forcing the vascular physician to renegotiate the arterial pathway with a new catheter and guidewire combination.

An alternative catheter design is the "monorail" variant of the over-the-wire system such as that disclosed in U.S. Pat. No. 4,762,129 issued Aug. 9, 1988 to Bonzel. This catheter design utilizes a conventional inflation lumen plus a relatively short parallel guiding or through lumen located at its distal end and passing through the dilatation balloon. This design enables the short externally accessible monorail or guidewire lumen to be threaded over the proximal end of a pre-positioned guidewire without the need for docking a guidewire extension. Additionally, because the guidewire lumen is quite short the guidewire remains external to all portions of the catheter proximal to the distal portion of the catheter and frictional drag along the guidewire lumen reportedly is reduced. Thus, it is possible to recross an acutely closed lesion or to exchange balloon catheters without losing guidewire access or docking an extension wire.

However, in spite of this success a significant disadvantage associated with monorail dilatation catheters is the difficulty in steering the catheter along the guidewire through tortuous or convoluted vascular pathways. Because the guidewire is not supported within the catheter it is possible to wrap the distal end of the catheter around the guidewire as vascular curves and junctions are traversed. Additionally, though it is possible to remove the guidewire and leave the monorail catheter in position, it is virtually impossible to replace or exchange the guidewire if necessary as it is impossible to reengage the distal monorail guidewire lumen once it is positioned in the patient's body.

A more recent attempt at dealing with these problems is disclosed in U.S. Pat. No. 4,988,356 issued Jan. 29, 1991 to Cruttenden et al. This catheter and guidewire exchange system utilizes a connector fitting mounted on the proximal end of the catheter in conjunction with a longitudinally extending slit in the catheter shaft extending distally from the fitting along the length of catheter the guidewire lumen. A guide member mounted on the fitting directs the guidewire through the slit and into the guidewire lumen in response to relative movement of the guidewire or catheter. This system reportedly avoids the need for a long exchange wire as well as the problems of a monorail design yet it presents several drawbacks of its own. First, the additional exchange fitting adds complexity to the design and function of the catheter. Further, the added drag induced by the fitting as it spreads the slit during catheter movement reduces the feel and control of the catheter as it is advanced along the guidewire. Moreover, because the slit terminates at a position distally to the proximal end of the catheter it is not possible to completely remove the catheter from the guidewire in a simple procedure. Reengagement of the catheter on the guidewire is even more complex.

Accordingly, it is an object of the present invention to provide a dilatation balloon catheter design that can be fully exchanged easily without sacrificing guidewire access to a target lesion. It is a further object of the present invention to provide a dilatation catheter that facilities the exchange or replacement of a guidewire if necessary.

It is yet an additional object of the present invention to provide a dilatation catheter with all of the advantages and features of an over-the-wire design that also provides the ability to remove the catheter from a pre-positioned guidewire rapidly and simply without utilizing a guidewire extension or long exchange wire.

A concurrent objective is to provide such a dilation catheter that can be rapidly removed from a pre-positioned guidewire by a single physician without the need for cutting instruments or special fittings to slit or open the guidewire lumen.

SUMMARY OF THE INVENTION

These and other objects are achieved by the fully exchangeable, over-the-wire balloon catheter of the present invention which, in accordance with broad structural aspects thereof, includes a balloon and a tubular shaft having at least one longitudinally aligned lumen extending throughout the length of the catheter body and adapted to carry a guidewire. The catheter is capable of conversion to a rapid exchange mode through the provision of one or more breakaway features in accordance with the teachings of the present invention. In a first embodiment the guidewire lumen is provided with a longitudinal pull tab extending from the proximal end of the lumen along the majority of its length to a position proximal to the dilatation balloon. To remove the catheter the vascular physician simply grasps the pull tab at the proximal end of the catheter and tears off the breakaway portion of the catheter wall along the guidewire lumen to progressively expose the guidewire and remove the catheter from the exposed proximal guidewire end.

In an alternative embodiment of the present invention the tubular shaft of the catheter itself is provided with one or more linearly arrayed longitudinal breakaway segments beginning at the proximal end of the catheter body. The segments can be defined by circumferential tear lines formed at various, preferably regular, intervals along the length of the tubular catheter body. To remove the catheter from the guidewire the vascular physician simply breaks or tears the first proximal segment away from the proximal end of the catheter and removes it from the proximal end of the guidewire. The remaining catheter then is retracted along the guidewire to expose the next circumferential breakaway line enabling the physician to break off and remove the next breakaway segment in the sequence. This procedure is repeated until the distal end of the catheter is removed from the patient's body leaving the guidewire in place.

In an additional embodiment of the present invention both breakaway features are combined to produce a catheter having a longitudinal pull tab and at least one proximal breakaway segment. In this configuration the Y-connector commonly found at the proximal end of most dilatation catheters can be permanently affixed to the first longitudinal breakaway segment. At or near the circumferential tear line for this first breakaway segment the pull tab for the longitudinal breakaway element is located. To remove the catheter the vascular physician simply breaks away and removes the Y-connector and first breakaway segment and then rips the pull tab to progressively expose the guidewire and remove it from the guidewire lumen.

As those skilled in the art will appreciate, tearing the pull tab from the catheter body in either embodiment will simultaneously extract the catheter while exposing the guidewire. This zipping motion enables the physician to quickly and easily remove the catheter without assistance while retaining guidewire access.

Additional features of the catheter may include forming the distal portion of the catheter from relatively flexible low density materials as opposed to the preferably stiffer construction of the proximal majority of the device. Visual marking indices may be added to facilitate initial positioning and placement of the device and radiopaque markers for X-ray visualization may be incorporated adjacent to the inflation balloon as known in the art. Various stiffening elements including wires or a proximal hypotube may be incorporated into the apparatus to improve its pushability. However, such stiffening elements should be removable or configured to not interfere with the function of the breakaway elements.

Other features and advantages of the present invention will become apparent from the following detailed description, taken in conjunction with the accompanying drawings which illustrate, by way of example, the principles of the present invention.

BRIEF DESCRIPTION OF THE DRAWINGS

FIG. 1 is a partial fragmentary perspective view of a rapid exchange over-the-wire balloon catheter with breakaway feature illustrating the principles of the present invention.

FIG. 2 is an enlarged partial fragmentary view of the proximal portion of the rapid exchange over-the-wire balloon catheter of FIG. 1 illustrating the pull-tab breakaway element.

FIG. 3 is an enlarged partial fragmentary view of the rapid exchange over-the-wire dilation catheter of FIG. 1 further illustrating the operation of the pull-tab breakaway element.

FIG. 7 is a partial fragmentary perspective view of an alternative embodiment of the rapid exchange over-the-wire balloon catheter of the present invention illustrating an alternative breakaway element.

FIG. 8 is an enlarged partial fragmentary cross-sectional view taken along the line 8—8 of FIG. 7 illustrating an exemplary construction of the alternative breakaway element.

FIG. 9 is a partial fragmentary view in perspective of the rapid exchange over-the-wire balloon catheter of FIG. 7 illustrating the operation of the alternative breakaway element.

DETAILED DESCRIPTION

Figure 6:
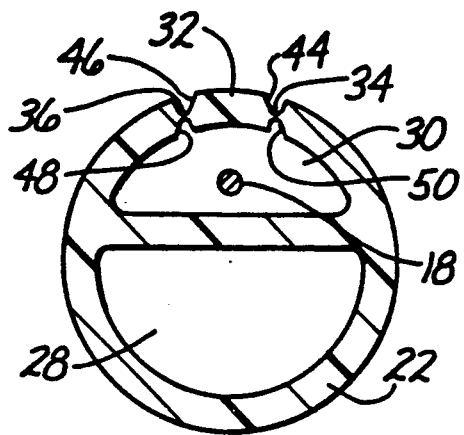
FIG. 6 is a cross-sectional view similar to that of FIG. 4 illustrating an alternative construction of the breakaway element.

Referring more particularly to the drawings in which similar elements are indicated by identical reference numerals. FIG. 1 illustrates an exemplary embodiment of the present invention including a catheter indicated generally by reference 10 mounted on a Y-connector 12 provided with an inflation port 14 and a compression hub 16 for sealing catheter 10 to Y-connector 12. A guidewire 18 extends proximally from Y-connector 12 and traverses the entire longitudinal extent of catheter 10. Catheter 10 includes an expandable or inflatable balloon 20 and a flexible, elongate tubular shaft 22 having a proximal end 24 adjacent compression hub 16 and a distal end 26 adjacent balloon 20.

Though not essential to the practice of the present invention, it is preferred that the proximal majority of shaft 22 be formed of relatively high density material to enhance its stiffness and pushability. Similarly, it is preferred that the remaining distal portion of shaft 22 be formed of relatively low density material to increase its flexibility and maneuverability through tortuous vascular pathways such as the coronary arteries. As those skilled in the art will appreciate, any form of medically acceptable secure joint is contemplated as being within the scope of the present invention for effecting this construction.

As shown in more detail in FIG. 2, catheter 10 is a dual lumen catheter provided with first and second lumens 28 and 30, respectively. Both lumens 28 and 30 extend throughout the longitudinal extent of tubular shaft 22 from proximal end 24 to distal end 26. Both lumens 28 and 30 are open at proximal end 24 and, in the exemplary embodiment of the present invention illustrated, first lumen 28 is connected in fluid conducting communication with inflation port 14 of Y-connector 12. At the distal end 26 of tubular shaft 22 first lumen 28 terminates in sealed fluid conducting communication with the interior of expandable balloon 20. Second lumen 30 is adapted to slidingly receive guidewire 18 throughout its longitudinal extent from proximal end 24 and through the interior of expandable balloon 20. Thus, guidewire 18 is able to extend beyond both Y-connector 12 at the proximal end of catheter 10 and balloon 20 at the distal end of catheter 10. In this manner, first lumen 28 functions as an inflation lumen for inflating and deflating balloon 20 while second lumen 30 functions as an over-the-wire guidewire lumen.

However, unlike conventional over-the-wire guidewire lumens, second lumen 30 is provided with a unique breakaway element. Referring again to the exemplary embodiment of the present invention illustrated in FIG. 2, the breakaway element shown is a tear strip 32 formed by a pair of longitudinally extending, generally parallel weakened wall sections 34 and 36 formed in the wall of guidewire lumen 30. Though not essential to the practice of the present invention, it is preferred that tear strip 32 be provided with a proximally disposed pull tab 38 formed at proximal end 24 of tubular shaft 22. In the embodiment of the present invention illustrated in FIG. 2, pull tab 38 is covered by compression hub 16 (shown in ghost line) so that catheter 10 functions as a conventional over-the-wire dilatation catheter. However, it is also contemplated as being within the scope of the present invention to mount pull tab 38 outside of compression hub 16.

Referring now to FIG. 3, the breakaway element of the present invention formed by tear strip 32 allows the vascular physician to progressively expose and remove guidewire 18 from lumen 30 in a simple and expeditious manner. In order to remove or exchange catheter 10 without disturbing the placement of guidewire 18 within a patient, the vascular physician simply grasps pull tab 38, preferably with forceps 40 or a similar tool to prevent slippage, and pulls tear strip 32 away from tubular shaft 22 from proximal end 24 toward distal end 26 in the direction of arrow 42. This simple motion functions to tear away weakened wall sections 34 and 36 to progressively expose guidewire 18 while simultaneously withdrawing catheter 10 from the patient's body along guidewire 18. Thus, the position of guidewire 18 within the patient can be maintained without utilizing docking extensions or extremely long external guidewire ends. Of equal importance, catheter 10 can be simply removed and exchanged by a single vascular physician with what is essentially a single motion.

As those skilled in the art also will appreciate, when pull tab 38 is originally disposed beneath compress hub 16 as shown in FIG. 2, the vascular physician will be required to remove compression hub 16 to expose pull tab 38. Similarly, where desired, complete removal of Y-connector 12 may be accomplished prior to pulling tear strip 32. However, this construction is not essential to the practice of the present invention.

Figure 5:
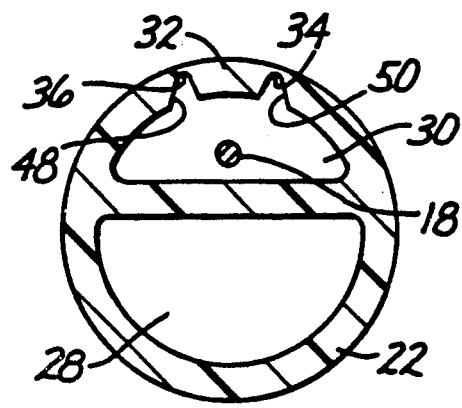
FIG. 5 is a cross-sectional view similar to that of FIG. 4 illustrating an alternative construction of the breakaway element.
Figure 4:
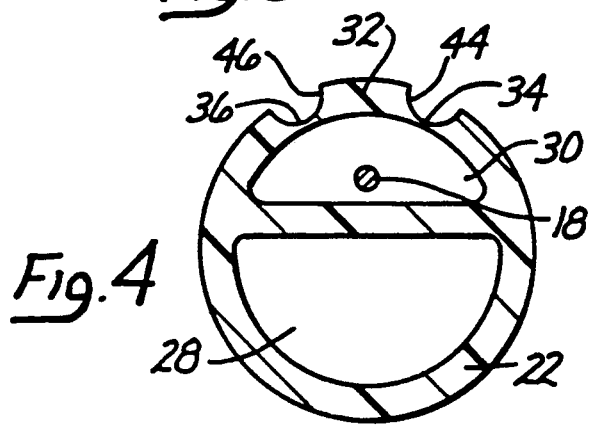
FIG. 4 is a cross-sectional view of the dilation catheter of FIG. 1 as seen along the line 4—4.

The formation of tear strip 32 and its associated weakened wall sections 34 and 36 may be formed in a variety of ways as known in the art. As shown in FIGS. 4, 5 and 6, it is possible to form the breakaway element of tear strip 32 by casting, cutting or extruding longitudinally extending, generally parallel external grooves 44 and 46 in the wall of lumen 30 to define weakened wall sections 34 and 36, respectively. Alternatively, as shown in FIG. 5, internal grooves 48 and 50 may be formed on the internal surface of lumen 30 to define weakened wall sections 34 and 36. Similarly, as illustrated in FIG. 4, combinations of external grooves 44 and 46 in conjunction with internal grooves 48 and 50 may be provided to form tear strip 32. It should be noted that the cross section of grooves 44 through 50 may vary from the arcuate configuration of grooves 44 and 46 to the angular configuration of grooves 48 and 50. Additionally, it is also contemplated as being within the scope of the present invention to replace the longitudinal external or internal grooves with partial cuts through the wall of lumen 30. Equivalent constructions are also contemplated as being within the scope of the present invention.

Turning now to FIG. 7, an alternative embodiment of the present invention is illustrated having a different breakaway element to facilitate the rapid removal or exchange of the catheter. The underlying catheter construction of this alternative embodiment is essentially identical to that of the embodiment previously discussed. Y-connector 12 having inflation port 14 is affixed to the proximal end 24 of the tubular shaft 22 by means of a suitable fitting such as compression hub 16. However, unlike the previously discussed embodiment of the present invention, the breakaway element of the catheter in this alternative embodiment is formed of one or more tubular breakaway segments 52, 54 and 56 linearly arrayed along tubular member 22 from proximal end 24 toward the distal end of the catheter (not shown). Each tubular breakaway segment is defined by its respective distally disposed circumferential tear line 58, 60 and 62 formed in the wall of tubular shaft 22.

As shown in the cross section of FIG. 8, circumferential tear line 58 defining the distal end of tubular breakaway segment 52 is formed from a circumferential weakened wall section 64 formed in tubular shaft 22. As with the previously discussed embodiment of the present invention, the circumferential weakened wall section 64 may be formed in a variety of manners including the hemispherical external groove illustrated in FIG. 8. Thus, internal grooves, combinations of internal and external grooves, partial circumferential cuts and the like may be utilized to practice the present invention.

It should also be noted that in this embodiment of the present invention tubular shaft 22 is illustrated as a single lumen catheter provided with a dual function lumen 66 that serves as both an inflation lumen and a guidewire lumen adapted to receive guidewire 18. Thus, it should be emphasized that the present invention is not restricted to single or dual lumen catheters. Rather, the present invention is applicable to single and multiple lumen catheters.

FIG. 9 illustrates the operation of the alternative tubular breakaway segments of the present invention. When the vascular physician wishes to remove the catheter from a patient while leaving guidewire 18 in place he or she simply grasps the proximally disposed breakaway segment such as segment 52 and snaps the first distally disposed circumferential tear line, line 58 in the embodiment shown, to break away the first tubular breakaway element from the distally remaining portions of the catheter. This short breakaway segment then is pulled from guidewire 18 in the direction of arrow 68 and discarded. The remaining catheter is then pulled along guidewire 18 in the direction of arrow 68 until the next sequential circumferential tear line is exposed outside of the patient's body. Thus, when tubular breakaway element 54 and circumferential tear line 60 are in position outside of the patient's body the vascular physician simply snaps tear line 60 and slides tubular breakaway segment 54 off guidewire 18 in the same manner as with segment 52. This process is repeated until a sufficient portion of the catheter has been progressively removed to a point where the entire catheter can be pulled from guidewire 18 without disturbing the position of guidewire 18 within the patient's body.

Figure 10:
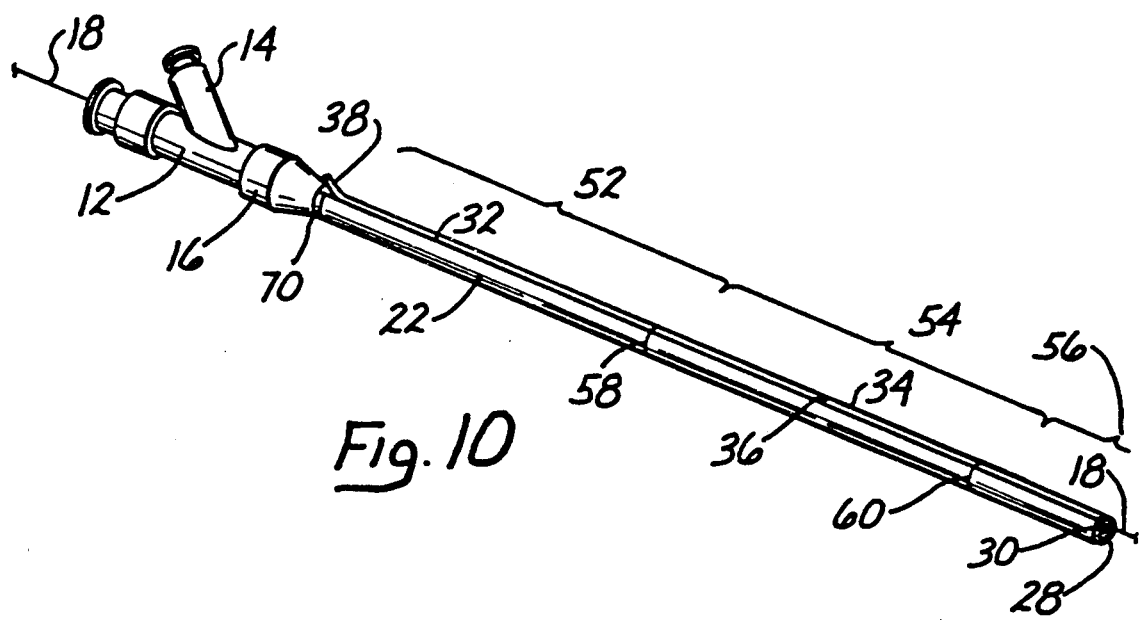
FIG. 10 is a partial fragmentary perspective view of an additional alternative embodiment of the rapid exchange over-the-wire balloon catheter with a combined breakaway feature illustrating the principles of the present invention.

An additional alternative embodiment of the present invention is illustrated in FIG. 10. This embodiment combines all of the previously discussed features in a single catheter design. Thus, tubular shaft 22 is provided with a tear strip 32 defined by longitudinally extending parallel weakened wall segments 34 and 36 (pull tab 38 is illustrated in a position outside of compression hub 16 as previously discussed) in addition to tubular breakaway segments 52, 54 and 56 defined by distally disposed circumferential tear lines 58, 60 and 62, respectively. As an additional feature, proximal circumferential tear line 70 is provided adjacent to compression hub 16 and pull tab 38. This proximal circumferential tear line enables the vascular surgeon to snap off Y-connector 12 in a quick and easy preliminary step prior to grasping pull tab 38 and ripping tear strip 32 to progressively expose guidewire 18 while removing the catheter from the patient's body. Then, if desired, tubular breakaway segments 52, 54 and the like may be snapped off and discarded as the catheter is removed to assist the vascular physician in controlling the apparatus during catheter removal or exchange.

In this manner, the various embodiments of the over-the-wire dilatation catheter of the present invention provide the vascular physician with the ability to remove or exchange catheters without compromising guidewire access to a target lesion. Of equal importance, the apparatus of the present invention does not require unique materials or construction techniques. Rather, the presently available construction techniques of tubular extrusion, etching, cutting and fusing are suitable for the manufacture of the present invention. Similarly, each of the embodiments of the present invention discussed herein may be formed from a variety of surgically acceptable flexible materials as known in the art. However, it is preferred that the proximal portion of tubular shaft 22 be formed of a relatively high density material such as 90/10 polyethylene to provide added pushability and control in placing the catheter within a vascular pathway. For enhanced flexibility and maneuverability at the distal end of the catheter it is preferred that the remaining distal portion of the tubular shaft be formed of relatively low density material such as 70/30 polyethylene. These two materials may be fused together using a radio frequency generator or heat. Preferably, the catheter of the present invention will have an overall length ranging from approximately 100 cm to 160 cm as known in the art.

Additionally, it should be appreciated that various stiffening elements may be utilized in conjunction with the dilatation catheter of the present invention. For example, the proximal portion of tubular shaft 22 may be stiffened utilizing wires (not shown) or flexible metal tubes known as "hypotubes" (not shown) which are disposed along its longitudinal extent as known in the art. However, such stiffening elements should be removable to avoid interference with the operation of the breakaway element or elements. It should be appreciated that these exemplary materials, dimensions and construction techniques are illustrative of the principles of the present invention and that other alternative materials, dimensions and construction techniques may be utilized within the scope of the present invention.

Similarly, in closing it is to be understood that the embodiments of the invention disclosed herein are illustrative of the principles of the invention and that other modifications may be employed which are within the scope thereof. Thus, by way of example, but not of limitation, the catheter may be provided with additional through lumens to compliment the guidewire and/or inflation lumens discussed. Similarly, the pull tab on the longitudinal rip seam can be replaced with a hook or eyelet to facilitate grasping and manipulation of the tear strip. Alternatively, the proximal end of the longitudinal tear strip may be permanently affixed to a breakaway Y-connector in place of the pull tab. Accordingly, the present invention is not limited to that precisely as shown and described in the specification.

What is claimed is:

1. A rapid exchange over-the-wire catheter for use in combination with a guidewire which has been positioned at a target site in a patient's body, said catheter comprising:
    a tubular shaft having a proximal end, a distal end, and at least one lumen adapted to receive said guidewire; and
    a tear strip longitudinally disposed in said tubular shaft along said lumen from said proximal end toward said distal end for progressively removing said tear strip from said tubular shaft from said proximal end toward said distal end to expose said guidewire and to allow said catheter to be removed from said guidewire while maintaining said guidewire in said desired position.

2. The rapid exchange over-the-wire dilation catheter of claim 1 wherein said tear strip is formed from a plurality of longitudinally extending generally parallel grooves formed in said tubular shaft.

3. The rapid exchange over-the-wire dilatation catheter of claim 2 wherein said grooves are provided external to said tubular shaft.

4. The rapid exchange over-the-wire dilatation catheter of claim 2 wherein said grooves are provided internal to said tubular shaft.

5. The rapid exchange over-the-wire catheter of claim 1 further comprising an expandable balloon disposed adjacent to said distal end.

6. The rapid exchange over-the-wire catheter of claim 1 wherein said tear strip is formed form a plurality of longitudinally extending generally parallel weakened wall segments in said lumen.

7. The rapid exchange over-the-wire catheter of claim 1 further comprising a pull tab formed in the proximal end of said tear strip.

8. A method for rapidly removing an over-the-wire catheter from a guidewire positioned within the body of a patient, said method comprising the steps of:
    providing the rapid exchange over-the-wire catheter of claim 6;
    threading a guidewire along the longitudinal extent of the lumen of said catheter;
    advancing said catheter and guidewire combination into a desired position within the body of a patient;
    performing a surgical procedure with said catheter;
    withdrawing said catheter along said guidewire by pulling the tear strip along said lumen form the proximal end of said catheter toward the distal end of said catheter to progressively expose said guidewire until the distal portion of said catheter is outside the body of said patient; and
    removing the remaining portion of said catheter from said guidewire.

9. A rapid exchange over-the-wire catheter for use in combination with a guidewire, said catheter comprising:
    a tubular shaft having a proximal end, a distal end, a lumen adapted to receive said guidewire; and
    at least one tubular breakaway segment proximally disposed on said tubular shaft for progressively exposing and removing said guidewire form said proximal end toward said distal end.

10. The rapid exchange over-the-wire catheter of claim 9 wherein said at least one tubular breakaway segment is defined by a distally disposed circumferential tear line provided in said tubular shaft.

11. The rapid exchange over-the-wire catheter of claim 10 wherein said circumferential tear line is formed from a circumferential groove formed in said tubular shaft.

12. The rapid exchange over-the-wire catheter of claim 10 wherein said circumferential tear line is formed from a circumferential weakened wall segment provided in said tubular shaft.

13. A method for rapidly removing an over-the-wire catheter from a guidewire positioned within the body of a patient, said method comprising the steps of:
    providing the rapid exchange over-the-wire catheter of claim 9;
    threading a guidewire along the longitudinal extent of the lumen of said catheter;
    advancing said catheter and guidewire combination into a desired position within the body of a patient;
    performing a surgical procedure with said catheter;
    withdrawing said catheter along said guidewire by sequentially snapping off each of said tubular breakaway segments form said proximal end towards said distal end of said catheter until the distal portion of said catheter is outside the body of said patient; and
    removing the remaining portion of said catheter from said guidewire.

14. A rapid exchange over-the-wire dilation catheter for use in combination with a guidewire, said catheter comprising:
    a tubular shaft having a proximal end, a distal end, and at least one lumen adapted to receive said guidewire, said tubular shaft being formed with at least one circumferential tear strip disposed between said proximal and distal end of said tubular shaft, said tear strip being operable for disecting a proximal portion of said tubular shaft from a distal portion of said tubular shaft allowing removal of said guidewire form said lumen; and an expandable dilation balloon disposed adjacent to said distal end.

15. The rapid exchange over-the-wire dilation catheter of claim 14 wherein said at least one tubular tear strip is defined by a circumferential tear line provided in said tubular shaft.

16. The rapid exchange over-the-wire dilation catheter of claim 15 wherein said circumferential tear line is formed from a circumferential groove formed in said tubular shaft.

* * * * *